United States Patent
Liu et al.

(10) Patent No.: US 11,485,949 B2
(45) Date of Patent: Nov. 1, 2022

(54) MICROORGANISM INOCULATION DEVICE

(71) Applicant: Binlu Liu, Qingdao (CN)

(72) Inventors: Binlu Liu, Qingdao (CN); Lu Xue, Qingdao (CN)

(73) Assignee: Binlu Liu ( * ) Notice: Subject to any disclaimer, the term of this patent is extended or adjusted under 35 U.S.C. 154(b) by 42 days.

(21) Appl. No.: 17/155,176

(22) Filed: Jan. 22, 2021

(65) Prior Publication Data
US 2022/0033754 A1  Feb. 3, 2022

(30) Foreign Application Priority Data

Jul. 31, 2020 (CN) .......................... 202010762797.4

(51) Int. Cl.
| C12M 1/32 | (2006.01) |
| C12M 3/00 | (2006.01) |
| C12M 1/26 | (2006.01) |
| B01L 9/02 | (2006.01) |
| B01L 9/00 | (2006.01) |
| G01N 35/10 | (2006.01) |
| G01N 1/14 | (2006.01) |
| C12M 1/30 | (2006.01) |
| C12M 1/36 | (2006.01) |

(52) U.S. Cl.
CPC ............... *C12M 33/06* (2013.01); *B01L 9/02* (2013.01); *B01L 9/52* (2013.01); *C12M 1/26* (2013.01); *C12M 1/265* (2013.01); *C12M 1/268* (2013.01); *C12M 23/48* (2013.01); *C12M 33/02* (2013.01); *C12M 33/04* (2013.01); *C12M 41/48* (2013.01); *G01N 35/1009* (2013.01); *G01N 35/1065* (2013.01); *G01N 2001/1427* (2013.01); *G01N 2001/1436* (2013.01)

(58) Field of Classification Search
CPC ........ C12M 33/06; C12M 1/26; C12M 1/265; C12M 1/268; C12M 23/48; C12M 33/02; C12M 33/04; C12M 41/48; B01L 9/02; B01L 9/52; G01N 35/1009; G01N 35/1065; G01N 2001/1427; G01N 2001/1436
See application file for complete search history.

(56) References Cited

U.S. PATENT DOCUMENTS

| 4,135,561 A * | 1/1979 | Senelonge | ......... G01N 35/1065 141/234 |
| 5,226,462 A * | 7/1993 | Carl | ..................... G01N 35/028 141/180 |

* cited by examiner

Primary Examiner — Samuel P Siefke
Assistant Examiner — Henry H Nguyen
(74) Attorney, Agent, or Firm — McDonald Hopkins LLC

(57) ABSTRACT

Disclosed is a microorganism inoculation device, which comprises a workbench, wherein support columns are provided on the upper surface of the workbench, a limiting plate is provided in the middle part of the supporting column, an injection head is provided in the middle part of the limiting plate, an air cylinder is provided in the middle part of the lower surface of the workbench, a piston rod of the air cylinder is fixedly connected with the middle part of the upper surface of a lifting plate, guide rods are provided on the upper surface of the lifting plate, the upper end of the guide rod is fixedly connected with a tray, the left and right sides of the upper surface of the tray are fixedly connected with the lower part of a fixed bracket, the middle part of the injection head is slidably connected with the limiting plate.

9 Claims, 5 Drawing Sheets

MICROORGANISM INOCULATION DEVICE

CROSS-REFERENCE TO RELATED APPLICATION

This application claims priority to Chinese Patent Application No. 202010762797.4 filed on Jul. 31, 2020 and entitled "MICROORGANISM INOCULATION DEVICE," which is incorporated by reference herein its entirety.

TECHNICAL FIELD

The present disclosure relates to the technical field of microorganisms, in particular to a microorganism inoculation device.

BACKGROUND

Microorganisms comprise a large group of organisms such as bacteria, viruses, fungi, some small protozoa, microalgae, etc., which are small and closely related to human beings. Many kinds of beneficial and harmful microorganisms are included, and many fields such as food, medicine, industry and agriculture, environmental protection, sports and so on are involved. In Chinese textbooks, microorganisms are divided into the following eight categories: bacteria, viruses, fungi, actinomycetes, rickettsia, mycoplasma, chlamydia and spirochete. Some microorganisms are visible to the naked eye, such as mushrooms, ganoderma lucidum, shiitake and so on. There is a kind of microorganisms which is "a non-cellular organism" consisted of a few components such as nucleic acids and proteins. Inoculation is the terminology of microbiology and the terminology of edible fungi cultivation. Inoculation is one of the key links in the production of edible fungi, which is also referred to as sowing.

Chinese patent (Publication No.: CN210237617U) discloses a microorganism inoculation device, which comprises a plurality of inoculation needles installed in a cover barrel, wherein the cover barrel consists of an upper cover body and a lower cover body, the upper cover body and the lower cover body are clamped and fixed with each other, a clamping mechanism is installed on the upper cover body, the inoculation needles are installed on the clamping mechanism, each inoculation needle is clamped with a pressing rod, the upper end of the pressing rod penetrates through the upper cover body and extends above the upper cover body, a connecting plate is fixedly installed at the lower end of each pressing rod, a spring is fixedly installed between the connecting plate and the upper cover body, the lower cover body is provided with a plurality of second through holes which correspond to the inoculation needles one by one, and the diameter of the second through holes is larger than the width of the inoculation needles. The advantages are that the inoculation operation can be quickly completed when the device performs inoculation for multiple times, the time spent for inoculation for multiple times is shortened, the operation speed of inoculation for multiple times is increased, and the inoculation operation is simpler, but the device can only inoculate one kind of microorganism at a time, and it is inconvenient to use in the comparative test, so that the device needs to be improved.

SUMMARY

The present disclosure provides a microorganism inoculation device, which solves the problems in the above background.

To achieve the above purpose, the present disclosure provides the following technical scheme.

A microorganism inoculation device comprises a workbench, wherein support columns are provided on the left and right sides of the upper surface of the workbench, a limiting plate is provided in the middle part of the support columnd, and an injection head is provided in the middle part of the limiting plate, wherein an air cylinder is provided in the middle part of the lower surface of the workbench, a piston rod of the air cylinder is fixedly connected with the middle part of the upper surface of a lifting plate, guide rods are provided on the left and right sides of the upper surface of the lifting plate, the upper end of the guide rod is fixedly connected with a tray, the left and right sides of the upper surface of the tray are fixedly connected with the lower part of a fixed bracket, the middle part of the injection head is slidably connected with a limiting plate, the upper part of the injection head is provided with a retaining edge, the left side of the retaining edge is provided with a nut, the middle part of the nut is threadedly connected with a limit screw rod, the lower part of the rear side of the injection head is provided with a feed inlet, the lower end of the injection head is provided with an injection port, the middle part of the injection head is slidably connected with the side of the piston of the injection head, the middle part of the upper surface of the piston is fixedly connected with the lower end of an ejector rod, the upper end of the ejector rod is fixedly connected with the middle part of the lower surface of a top plate, and the left and right ends of the the top plate are each fixedly connected with the upper end of the corresponding one of the support columns.

As a preferred technical scheme of the present disclosure, three injection heads are provided in the middle part of the limiting plate.

As a preferred technical scheme of the present disclosure, the upper end of the limit screw rod is provided with a rotating wheel.

As a preferred technical scheme of the present disclosure, a connecting pipe is provided at the rear end of the feed inlet.

As a preferred technical scheme of the present disclosure, the lower part of the injection head is provided with a limiting ring.

As a preferred technical scheme of the present disclosure, the cross section of the fixed bracket is U-shaped, and the upper part of the fixed bracket is provided with a yielding port matched with the injection head.

As a preferred technical scheme of the present disclosure, the tray is annular, a placing ring is provided in the middle part of the tray, and the inner diameter of the lower part of the placing ring is smaller than the inner diameter of the upper part.

As a preferred technical scheme of the present disclosure, the middle part of the guide rod is slidably connected with the left and right sides of the workbench.

As a preferred technical scheme of the present disclosure, support legs are provided on the left and right sides of the lower surface of the workbench.

As a preferred technical scheme of the present disclosure, an O-ring is provided outside the piston.

The present disclosure has the following advantages.

The present disclosure is suitable for a microorganism inoculation device, and the device is provided with a limit screw rod for controlling the up-and-down moving height of the injection head, so that the internal volume of the injection head can be adjusted, and the capacity of inoculated microorganisms can be individually controlled. The control of the whole device is relatively simple. After the limit screw rod is adjusted, only the Petri dish needs to be placed inside the device and the air cylinder is started. The whole device has simple operation and high working efficiency, and is suitable for batch production.

BRIEF DESCRIPTION OF THE DRAWINGS

In order to explain the embodiments of the present disclosure or the technical scheme in the prior art more clearly, the drawings required in the embodiments or the description of the prior art will be briefly introduced hereinafter. Obviously, the drawings in the following description are only some embodiments of the present disclosure, and other drawings can be obtained according to these drawings for those skilled in the art without paying creative labor.

Figure 1:
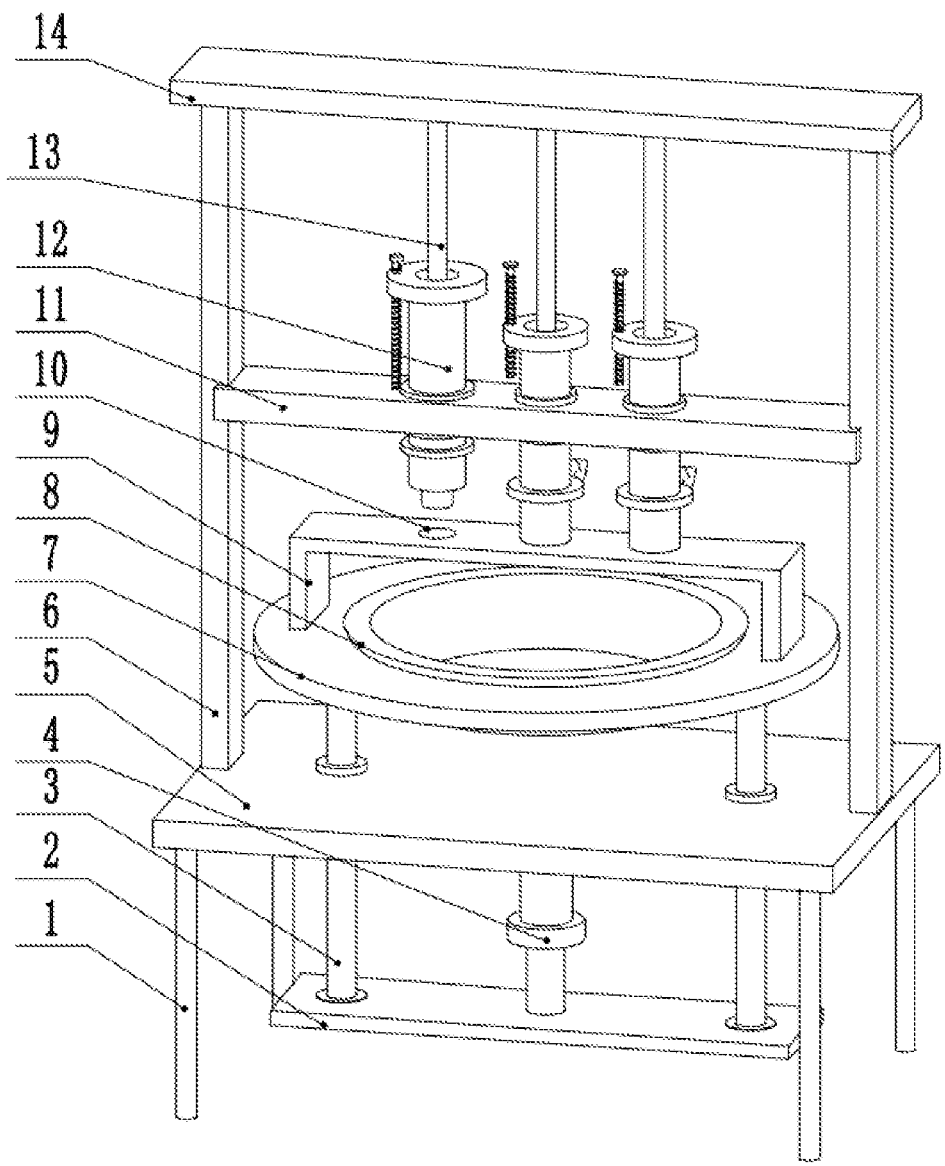
FIG. 1 is a schematic structural diagram of a microorganism inoculation device.
Figure 2:
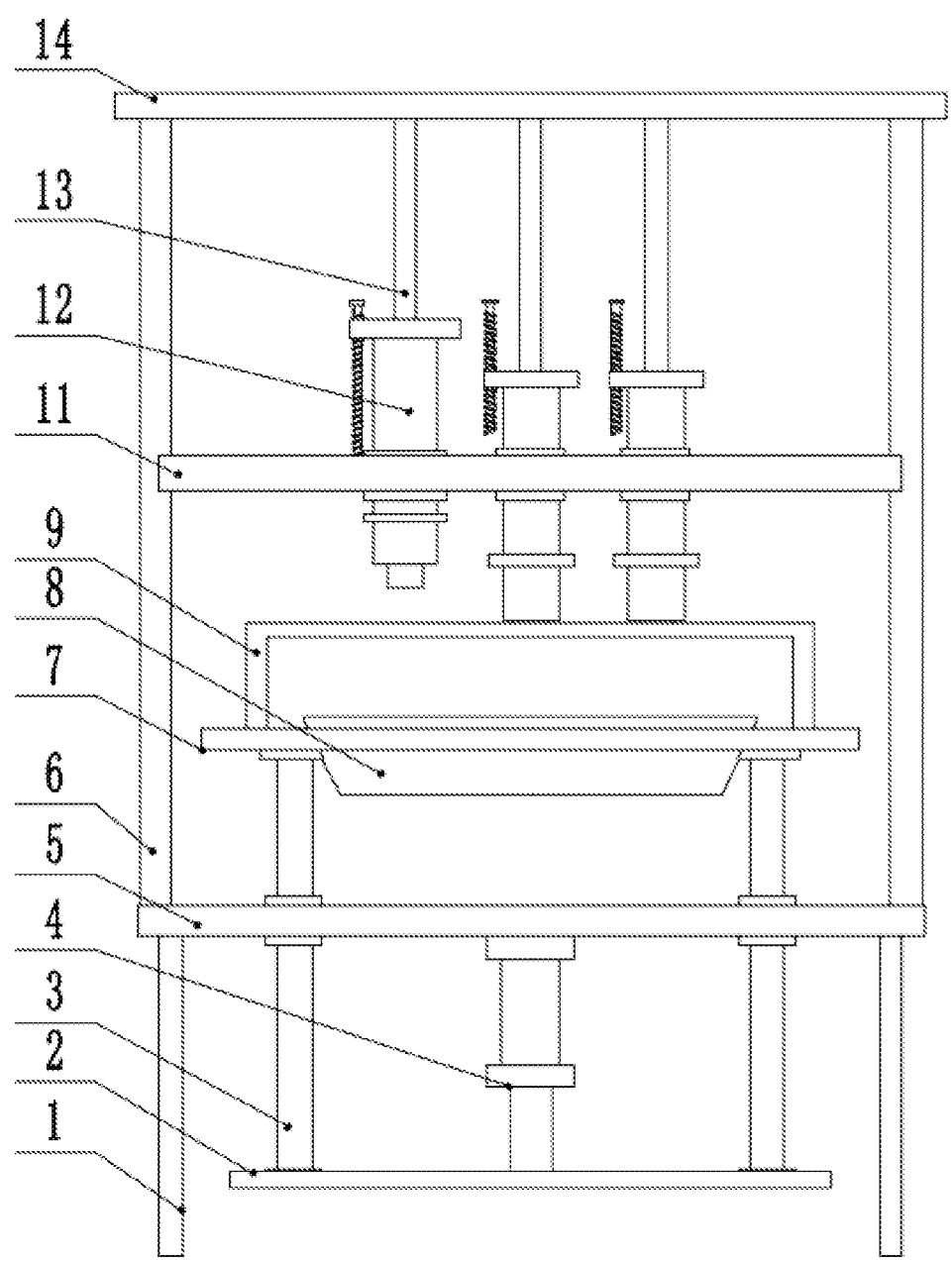
FIG. 2 is a front view of a microorganism inoculation device.
Figure 3:
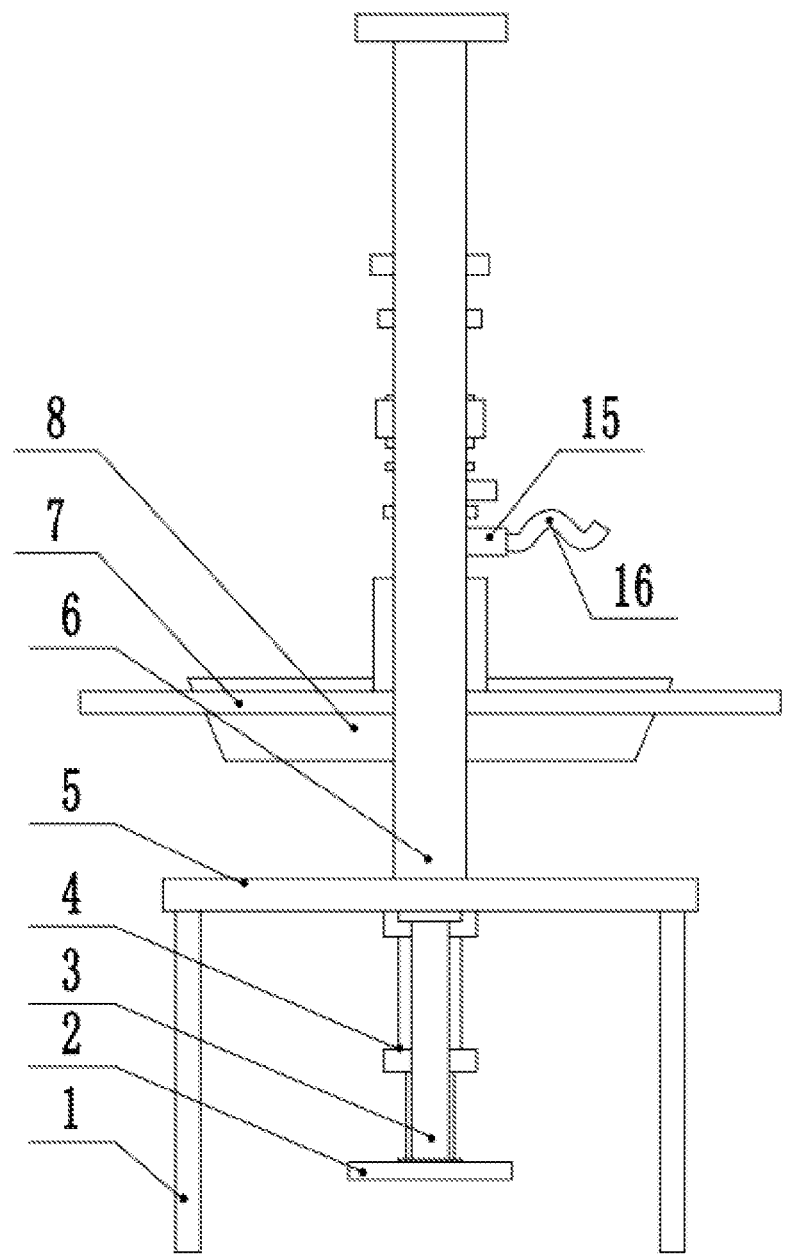
FIG. 3 is a right view of a microorganism inoculation device.
Figure 4:
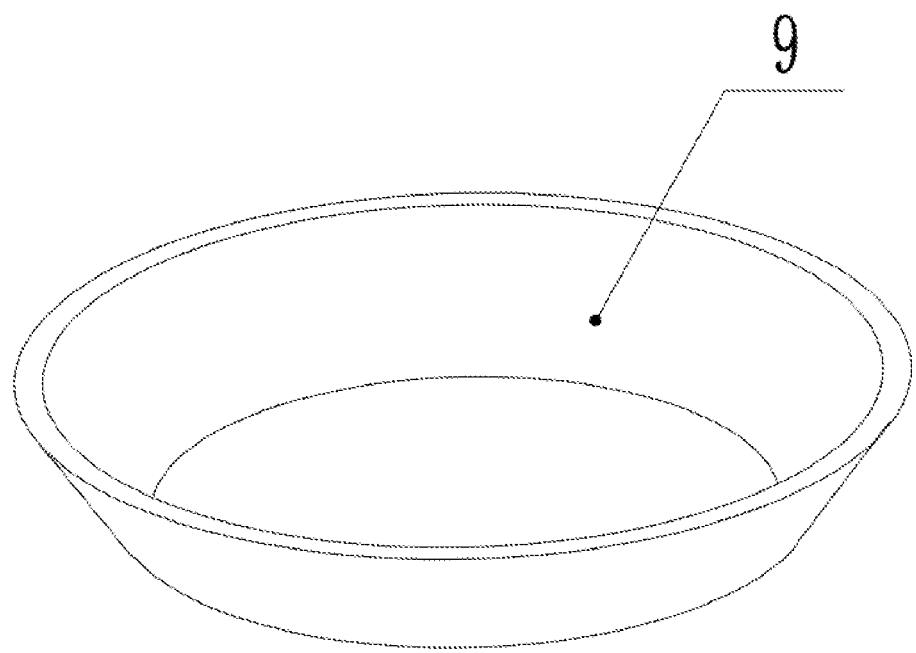
FIG. 4 is a schematic structural diagram of a placing ring in a microorganism inoculation device.

In the figures: 1. Support leg; 2. Lifting plate; 3. Guide rod; 4. Air cylinder; 5. Workbench; 6. Support column; 7. Tray; 8. Placing ring; 9. Fixed bracket; 10. Yielding port; 11. Limiting plate; 12. Injection head; 13. Ejector rod; 14. Top plate; 15. Feed inlet; 16. connecting pipe; 17. Injection port; 18. limiting ring; 19. O-ring; 20. Piston; 21. Limit screw rod; 22. Retaining edge; 23. Rotating wheel; 24. Nut

DETAILED DESCRIPTION

The technical scheme in the embodiments of the present disclosure will be described clearly and completely with reference to the drawings in the embodiments of the present disclosure. Obviously, the described embodiments are some embodiments of the present disclosure, rather than all of the embodiments. Based on the embodiments of the present disclosure, all other embodiments obtained by those skilled in the art without paying creative labor belong to the scope of protection of the present disclosure.

Embodiment 1

Referring to FIGS. 1-5, a microorganism inoculation device comprises a workbench 5, wherein support columns 6 are provided on the left and right sides of the upper surface of the workbench 5. A limiting plate 11 is provided in the middle parts of the support columns 6. An injection head 12 is provided in the middle part of the limiting plate 11. Three injection heads 12 are provided in the middle part of the limiting plate 11. An air cylinder 4 is provided in the middle part of the lower surface of the workbench 5. A piston rod of the air cylinder 4 is fixedly connected with the middle part of the upper surface of a lifting plate 2. Guide rods 3 are provided on the left and right sides of the upper surface of the lifting plate 2. The middle part of the guide rod 3 is slidably connected with the left and right sides of the workbench 5. The upper end of the guide rod 3 is fixedly connected with a tray 7. The left and right sides of the upper surface of the tray 7 are fixedly connected with the lower part of a fixed bracket 9. The tray 7 is annular. A placing ring 8 is provided in the middle part of the tray 7. The inner diameter of the lower part of the placing ring 8 is smaller than the inner diameter of the upper part. By gradually reducing the diameter, the Petri dish can be directly centered in the placing ring 8 after being placed in the placing ring 8. Because the tray 7 will descend when the Petri dish is taken out later, the bottom of the Petri dish will contact with the upper surface of the workbench 5 in the descending process, so that the Petri dish can be pushed out from the placing ring 8 by the workbench 5, thus making it more convenient for operators to take and place the Petri dish in the placing ring 8.

The middle part of the injection head 12 is slidably connected with a limiting plate 11. The upper part of the injection head 12 is provided with a retaining edge 22. The left side of the retaining edge 22 is provided with a nut 24. The middle part of the nut 24 is threadedly connected with a limit screw rod 21. The upper end of the limit screw rod 21 is provided with a rotating wheel 23. The lower part of the rear side of the injection head 12 is provided with a feed inlet 15. A connecting pipe 16 is provided at the rear end of the feed inlet 15. The free end of the connecting pipe 16 can be connected to a raw material bin in which microorganism stock solution is stored. A one-way valve is provided inside the feeding port 15, so that microorganisms can only enter the injection head 12 through the raw material bin, but cannot flow back from the injection head 12 to the raw material bin. For realizing the subsequent feeding step, the lower end of the injection head 12 is provided with an injection port 17. The middle part of the injection head 12 is slidably connected with the side of the piston 20 of the injection head 12. The middle part of the upper surface of the piston 20 is fixedly connected with the lower end of an ejector rod 13. The upper end of the ejector rod 13 is fixedly connected with the middle part of the lower surface of a top plate 14. The left and right ends of the the top plate 14 are each fixedly connected with the upper end of the corresponding one of the support columns 6. The lower part of the injection head 12 is provided with a limiting ring 18. The cross section of the fixed bracket 9 is U-shaped, and the upper part of the fixed bracket 9 is provided with a yielding port 10 matched with the injection head 12. The diameter of the injection port 17 is smaller than the yielding port 10, and the outer diameter of the injection head 12 is larger than the yielding port. Therefore, when the fixed bracket 9 contacts the bottom of the injection head 12, the injection port 17 will be inserted into the yielding port 10, and the injection head 12 will be stuck, so that the injection head 12 will be pushed up and down by the fixed bracket 9, and the fixed bracket 9 will not affect the extrusion of microorganisms from the injection port 17.

Embodiment 2

Figure 5:
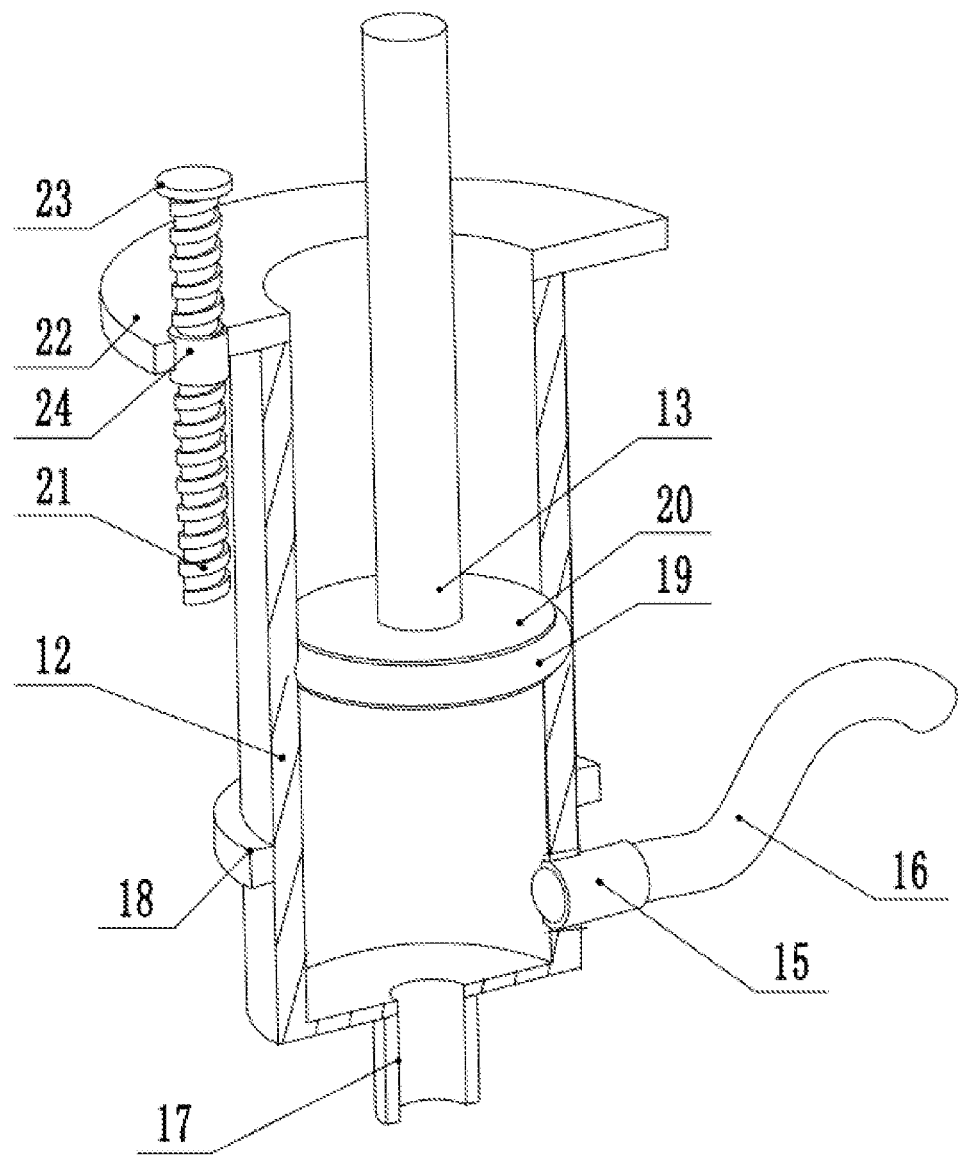
FIG. 5 is a cross-sectional diagram of an injection head in a microorganism inoculation device.

Referring to FIG. 5, the other contents of this embodiment are the same as those of the first embodiment, except that an O-ring 19 is provided outside the piston 20. In order to improve the sealing effect between the piston 20 and the inner wall of the injection head 12, an O-ring 19 is provided outside the piston 20. By providing the O-ring 19, the machining accuracy of the piston 20 and the inner wall of the injection head 12 can be reduced. After the device works for a period of time, the sealing effect of the injection head 12 can be ensured by replacing the O-ring 19.

In the implementation process of the present disclosure, the connecting pipe 16 is connected with the raw material bin, so that the raw material bin in which different microorganisms are placed is connected with different injection heads 12. The limit screw rod 21 is rotated, and the limit screw rod 21 is threadedly connected with the nut 24, so that the position relationship between the limit screw rod 21 and the retaining edge 22 is adjusted, so that the injection head 12 slides downward only under the action of gravity. The limit screw rod 21 limits the minimum descending height of the injection head 12. Therefore, the number of microorganisms stored in the injection head 12 can be controlled by custom. After the adjustment of the whole device is completed, the Petri dish for culturing microorganisms is placed in the placing ring 8. At this time, the air cylinder 4 is started, the piston rod of the air cylinder 4 contracts, the piston rod drives the lifting plate 2 to move upwards, and the lifting plate 2 drives the tray 7 and the fixed bracket 9 to move upwards, so that the Petri dish move upwards. After the fixed bracket 9 contacts the injection head 12, the injection port 17 at the lower end of the injection head 12 passes through the yielding port 10, and the fixed bracket 9 drives the injection head 12 to move upwards. At this time, the ejector rod 13 drives the piston 20 to keep its height constant. That is to say, at this time, the piston 20 moves downwards with respect to the injection head 12, and the piston 20 extrudes the microorganisms in the injection head 12 through the injection port 17. After being extruded from the injection port 17, the microorganisms fall on the Petri dish. Because the positions and heights of the three limit screw rods 21 are different, the fixed bracket 9 contacts with the three injection heads 12 successively, so that the microorganisms in the injection heads 12 are extruded on the Petri dish. Three bacterial colonies are formed on the Petri dish, which can be used for the later comparative test. After inoculation is completed, the air cylinder 4 is started reversely, the piston rod of the air cylinder 4 extends out, and the lifting plate 2 moves downward, so that the tray 7 and the fixed bracket 9 move downward and the fixed bracket 9 is separated from the injection head 12. At this time, the injection head 12 moves downward under the action of gravity until the left limit screw rod 21 contacts the limiting plate 11, the injection head 12 stops moving, and during the downward movement of the injection head 12, microorganisms are pumped into the injection head 12 through the feed inlet 15, so as to be used in the subsequent inoculation operation of the Petri dish. The present disclosure is suitable for a microorganism inoculation device, and the device is provided with a limit screw rod 21 for controlling the up-and-down moving height of the injection head 12, so that the internal volume of the injection head 12 can be adjusted, and the capacity of inoculated microorganisms can be individually controlled. The control of the whole device is relatively simple. After the limit screw rod 21 is adjusted, only the Petri dish needs to be placed inside the device and the air cylinder 4 is started. The whole device has simple operation and high working efficiency, and is suitable for batch production.

It is obvious to those skilled in the art that the present disclosure is not limited to the details of the above exemplary embodiments, and that the present disclosure can be realized in other specific forms without departing from the spirit or basic characteristics of the present disclosure. Therefore, the embodiments should be regarded as exemplary and non-limiting from any point of view. The scope of the present disclosure is defined by the appended claims rather than the above description. Therefore, it is intended to cover all changes falling within the meaning and range of equivalent elements of the claims in the present disclosure. Any reference signs in the claims should not be regarded as limiting the claims involved.

What is claimed is:

1. A microorganism inoculation device, comprising:

a workbench, wherein support columns are provided on left and right sides of an upper surface of the workbench, a limiting plate is provided in middle parts of the support columns, and three injection heads are provided in a middle part of the limiting plate, wherein an air cylinder is provided in a middle part of a lower surface of the workbench, a piston rod of the air cylinder is fixedly connected with a middle part of an upper surface of a lifting plate, guide rods are provided on left and right sides of the upper surface of the lifting plate, upper ends of the guide rods are fixedly connected with a tray, left and right sides of an upper surface of the tray are fixedly connected with a lower part of a fixed bracket, a middle part of each of the three injection heads is slidably connected with the limiting plate, an upper part of the injection head is provided with a retaining edge, a left side of the retaining edge is provided with a nut, a middle part of a nut is threadedly connected with a limit screw rod, a lower part of the rear side of a injection head is provided with a feed inlet, a lower end of the injection head is provided with an injection port, a middle part of the injection head is slidably connected with a side of a piston of the injection head, a middle part of an upper surface of the piston is fixedly connected with a lower end of an ejector rod, an upper end of the ejector rod is fixedly connected with a middle part of a lower surface of a top plate, and left and right ends of the the top plate are each fixedly connected with an upper end of the corresponding one of the support columns.

2. The microorganism inoculation device according to claim 1, wherein an upper end of the limit screw rod is provided with a rotating wheel.

3. The microorganism inoculation device according to claim 1, wherein a connecting pipe is provided at a rear end of the feed inlet.

4. The microorganism inoculation device according to claim 1, wherein a lower part of the injection head is provided with a limiting ring.

5. The microorganism inoculation device according to claim 1, wherein a cross section of the fixed bracket is U-shaped, and an upper part of the fixed bracket is provided with a plurality of yielding ports each of which is matched with a corresponding one of the injection heads.

6. The microorganism inoculation device according to claim 1, wherein the tray is annular, a placing ring is provided in a middle part of the tray, and an inner diameter of a lower part of the placing ring is smaller than an inner diameter of an upper part of the placing ring.

7. The microorganism inoculation device according to claim 1, wherein a middle part of each of the guide rods is slidably connected with a corresponding one of left and right sides of the workbench.

8. The microorganism inoculation device according to claim 1, wherein support legs are provided on a left and right sides of the lower surface of the workbench.

9. The microorganism inoculation device according to claim 1, wherein an O-ring is provided outside the piston.

* * * * *